United States Patent [19] [11] 4,061,643
Cragoe, Jr. et al. [45] Dec. 6, 1977

[54] CERTAIN 16-ARYLOXY-11,12-SECO-PROSTAGLANDINS

[75] Inventors: Edward J. Cragoe, Jr.; John B. Bicking, both of Lansdale, Pa.

[73] Assignee: Merck & Co., Inc., Rahway, N.J.

[21] Appl. No.: 721,734

[22] Filed: Sept. 9, 1976

Related U.S. Application Data

[60] Division of Ser. No. 587,924, June 18, 1975, Pat. No. 4,020,177, which is a continuation-in-part of Ser. No. 502,126, Aug. 30, 1974, abandoned.

[51] Int. Cl.² .................. C07D 307/54; C07D 213/30
[52] U.S. Cl. .......................... 260/295 R; 260/251 R; 260/332.2 R; 260/347.3; 260/347.4
[58] Field of Search ............ 260/347.3, 347.4, 295 R, 260/251 R, 332.2 R Primary Examiner—Henry R. Jiles
Assistant Examiner—Bernard Dentz
Attorney, Agent, or Firm—Thomas E. Arther; Harry E. Westlake, Jr.; Rudolph J. Anderson, Jr.

[57] ABSTRACT

This invention relates to aryloxy-, alkoxy-, arylthio-, and alkylthio-11,12-seco-prostaglandins and to processes for their manufacture. These compounds have prostaglandin-like activity and are particularly useful in fertility control such as for estrus synchronization in animals and postcoital contraceptive agents in humans.

10 Claims, No Drawings

CERTAIN 16-ARYLOXY-11,12-SECO-PROSTAGLANDINS

RELATIONSHIP TO OTHER APPLICATIONS

This is a division of application Ser. No. 587,924 filed June 18, 1975, now U.S. Pat. No. 4,020,177; which in turn is a continuation-in-part of application Ser. No. 502,126 filed Aug. 30, 1974, now abandoned.

SUMMARY OF THE INVENTION

This invention relates to novel aryloxy-, alkoxy-, arylthio-, and alkylthio-11,12-seco-prostaglandins and related substances. These compounds are represented by the following structural formula:

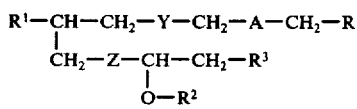

wherein R is selected from the group consisting of carboxy and a carboxy salt being formed from a pharmaceutically acceptable cation, such as metal cations derived from alkali metals, alkaline earth metals and amines such as ammonia, primary and secondary amines and quaternary ammonium hydroxides. Especially preferred metal cations are those derived from alkali metals, e.g., sodium, potassium, lithium, and the like, and alkaline earth metals, e.g., calcium, magnesium, and the like and other metals, i.e., aluminum, iron, and zinc.

Pharmaceutically acceptable cations derived from primary, secondary, or tertiary amines, or quaternary ammonium hydroxides are methylamine, dimethylamine, trimethylamine, ethylamine, N-methylhexylamine, benzylamine, α-phenethylamine, ethylenediamine, piperidine, morpholine, pyrrolidine, 1,4-dimethylpiperazine, ethanolamine, diethanolamine, triethanolamine, tris(hydroxymethyl)aminomethane, N-methylglucamine, N-methylglucosamine, ephedrine, procaine, tetramethylammonium hydroxide, tetraethylammonium hydroxide, benzyltrimethylammonium and and like.

R is also selected from alkoxycarbonyl (—COOAlk) wherein Alk is alkyl having 1–10 carbon atoms, carbamoyl (—CONH$_2$); substituted carbamoyl (—CONR$^4$R$^5$) wherein R$^4$ and R$^5$ are selected from the group consisting of hydrogen, lower alkyl having 1–4 carbon atoms and diloweralkylaminoalkyl having 4–7 carbon atoms; and carbazoyl (—CONHNH$_2$).

R$^1$ is selected from the group consisting of acetyl, propionyl, 1-hydroxyethyl, 1-hydroxypropyl and hydroxymethyl.

A is selected from the group consisting of methylene (—CH$_2$—) or oxygen (—O—).

Y is selected from the group consisting of ethylene, vinylene (particularly cis-vinylene), or ethynylene.

Z is selected from the group consisting of ethylene, vinylene (particularly trans-vinylene), or ethynylene.

R$^2$ is hydrogen or loweralkanoyl.

R$^3$ is O-R$^6$ or S-R$^6$ wherein R$^6$ is phenyl; substituted phenyl,

where X is halogen, trifluoromethyl, lower alkyl, lower alkoxy, dimethylamino, nitro, mesyl, lower alkanoyl, and the like attached o, m, or p, and n is 1 or 2, and where n is 2, X$_n$ may represent such groups as methylenedioxy; benzyl, or substituted benzyl,

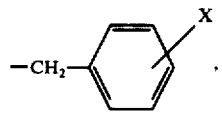

where X is as previously defined; pyridyl, pyrimidinyl, furfuryl, thenyl, and the like; or lower alkyl of 2 to 7 carbon atoms, straight chain or branched, or fluorinated alkyl.

BACKGROUND OF THE INVENTION

The compounds of formula I are described as 11,12-seco-prostaglandins because of their structural relationship to the naturally occurring prostaglandins.

The prostaglandins constitute a biologically prominent class of naturally occurring, highly functionalized C$_{20}$ fatty acids which are anabolized readily in a diverse array of mammalian tissues from three essential fatty acids; namely 8,11,14-eicosatrienoic acid, 5,8,11,14-eicosatetraenoic acid, and 5,8,11,14,17-eicosapentaenoic acid. Each know prostaglandin is a formula derivative of the parent compound, termed "prostanoic acid"; the latter is a C$_{20}$ fatty acid covalently bridged between carbons 8 and 12 such as to form a trans, vicinally-substituted cyclopentane in which the carboxybearing side chain is "alpha" or below the plane of the ring and the other side chain is "beta" or above the plane of the ring as depicted in formula III:

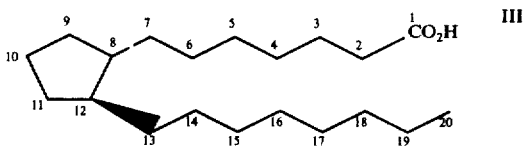

Although the prostaglandins were discovered independently in the mid-1930's by Goldblatt [J. Chem. Soc. Chem. Ind. Lond., 52, 1056 (1933)] in England and Von Euler [Arch. Exp. Path. Pharmark., 175, 78 (1934)] in Sweden, these complex natural products received little attention from the scientific community until the early 1960's which coincides with the advent of modern instrumentation (e.g., mass spectrometry) which, in turn, was requisite for their successful isolation and structural elucidation by Bergström and coleagues [see Angew. Chem. Int. Ed., 4, 410 (1965) and references cited therein for an account of this work]. Within the last decade, a massive international scientific effort has been expended in developing both biosynthetic and chemical routes to the protaglandins and, subsequently, in investigating of their biological activities. During this period, prostaglandins have been shown to occur extensively in low concentrations in a myriad of mammalian tissues where they are both rapidly anabolized and catabolized and to exhibit a vast spectrum of pharmacological activities including prominent roles in (a) functional hyperemia, (b) in inflammatory response, (c) the central nervous system, (d) transport of water and electrolytes, and (e) regulation of cyclic AMP. Further details concerning the prostaglandins can be found in recent reviews of their chemistry [J. E. Pike, Fortschr. Chem. Org. Naturst., 28, 313 (1970) and G. F. Bundy, A. Rep. in Med. Chem., 7, 157 (1972)], biochemistry [J. W. Hinman, A. Rev. Biochem., 41, 161 (1972)], pharmacology [J. R. Weeks, A. Rev. Pharm., 12, 317 (1972)], physiological significance [E. W. Horton, Physiol. Rev., 49, 122 (1969)], and general clinical application [J. W. Hinman, Postgrad. Med. J., 46, 562 (1970)].

The potential application of natural prostaglandins as medicinally useful therapeutic agents in various mammalian disease states is obvious but suffers from three formidable major disadvantages, namely, (a) prostaglandins are known to be rapidly metabolized in vivo in various mammalian tissues to a variety of metabolites which are devoid of the desired original biological activities, (b) the natural prostaglandins are inherently devoid of biological specificity which is requisite for a successful drug, and (c) although limited quantities of prostaglandins are presently produced by both chemical and biochemical processes, their production cost is extremely high; and, consequently, their availability is quite restricted.

Our interest has, therefore, been to synthesize novel compounds structurally related to the natural prostaglandins but with the following unique advantage: (a) simplicity of synthesis leading to low cost of production; (b) specificity of biological activity which may be either of a prostaglandin-mimicking or prostaglandin-antagonizing type; (c) enhanced metabolic stability. The combination of these advantages serves to provide effective, orally and parenterally active therapeutic agents for the treatment of a variety of human and animal diseases. Included are applications in renal, cardiovascular, gastrointestinal, respiratory, and reproductive systems, and in the control of lipid metabolism, inflammation, blood clotting, skin diseases, growth hormone release, selected cancers, and certain autoimmune diseases.

More specifically, in the clinic, prostaglandin agonists can function as agents for improving renal function (e.g., renal vasodilation, antihypertensives, anti-ulcer agents, agents for fertility control, anti-thrombotics, antiasthmatics, antilipolytics, antineoplastic agents, agents for the treatment of certain skin diseases, dwarfism, and autoimmune diseases.

Prostaglandin antagonists can function as antiinflammatory agents, anti-diarrheal agents, antipyretics, agents for prevention of premature labor, and agents for the treatment of headache.

The compounds of this invention are particularly useful in the area of fertility control. In animals, they can be used for estrus synchronization, and treatment of infertility due to persistence of luteal function. In humans, they can be used as postcoital contraceptive agents which function by induction of menses. Compounds of this invention which are particularly useful in fertility control are those where $R^1$ is 1-hydroxyethyl, 1-hydroxypropyl, or hydroxymethyl and Y is cis-vinylene.

Further, the compounds of this invention by virtue of their marked activity in inhibiting the aggregation of blood platelets are of potential usefulness as anti-thrombotic agents.

In addition, the compounds of this invention, especially those where $R^1$ is 1-hydroxyethyl, 1-hydroxypropyl, or hydroxymethyl, and Y is cis-vinylene, are potentially useful in the treatment of hypertension in humans. This is shown by the fact that said compounds are useful in lowering blood pressure in a strain of spontaneously hypertensive rats when the compounds are administered orally to the rats in doses of approximately 1.25 mg./kg. of test animal. An example of such a compound is 8-(1-hydroxyethyl)-12-hydroxy-13-(4-fluorophenoxy)-5-cis-tridecenoic acid.

The compounds of this invention can be administered either topically or systemically, i.e., intravenously, subcutaneously, intramuscularly, orally, rectally, or by aerosolization in the form of sterile implants for long action. They can be formulated in any of a number of pharmaceutical compositions and non-toxic carriers to this end.

The pharmaceutical compositions can be sterile injectable suspensions or solutions, or solid orally administrable pharmaceutically acceptable tablets or capsules; the compositions can also be intended for sublingual administration, or for suppository use. It is especially advantageous to formulate compositions in dosage unit forms for ease and economy of administration and uniformity of dosage. "Dosage unit form" as a term used herein refers to physically discrete units suitable as unitary dosages for animal and human subjects, each unit containing a predetermined quantity of active material calculated to produce the desired biological effect in association with the required pharmaceutical means.

Illustratively, a sterile injectable composition can be in the form of aqueous or oleagenous suspensions or solutions.

The sterile injectable composition can be aqueous or oleagenous suspension or solution. Suspensions can be formulated according to the known art using suitable dispersing and wetting agents and suspending agents. Solutions are similarly prepared from the salt form of the compound. For the laboratory animals, we prefer to use incomplete Freund's adjuvant or sterile saline (9%) as carrier. For human parenteral use, such as intramuscularly, intravenously, or by regional perfusion, the diluent can be a sterile aqueous vehicle containing a preservative; for example, methylparaben, propylparaben, phenol, and chlorobutanol. The aqueous vehicle can also contain sodium chloride, preferably in an amount to be isotonic; as well as a suspending agent, for example, gum arabic, polyvinyl pyrrolidone, methyl cellulose, acetylated monoglyceride (available commercially as Myvacet from Distillation Products Industry, a division of Eastman Kodak Company), monomethyl glyceride, dimethyl glyceride or a moderately high molecular weight polysorbitan (commercially available under the tradenames Tween or Span from Atlas Powder Company, Wilmington, Delaware). Other materials employed in the preparation of chemotherapeutic compositions containing the compound may include glutathione, 1,2-propanediol, glycerol and glucose. Additionally, the pH of the composition is adjusted by use of an aqueous solution such as tris(hydroxymethyl)aminomethane (tris buffer).

Oily pharmaceutical carriers can also be used, since they dissolve the compound and permit high doses. Mainly oily carriers are commonly employed in pharmaceutical use, such as, for example, mineral oil, lard, cottonseed oil, peanut oil, sesame oil, or the like.

It is preferred to prepare the compositions, whether aqueous or oils, in a concentration in the range of from 2–50 mg./ml. Lower concentrations require needless quantities of liquid. Higher concentrations than 50 mg./ml. are difficult to maintain and are preferably avoided.

Oral administration forms of the drug can also be prepared for laboratory animals or human patients. The same dosage levels can be used as for injectable forms. Generally, a solid unit dosage form can be prepared containing from 0.5 mg. to 25 mg. active ingredient.

Whatever the mode of administration, doses in the range of about 0.10 to 20 milligrams per kilogram of body weight administered one to four times per day are used, the exact dose depending on the age, weight, and condition of the patient, and the frequency and route of administration.

The low cost and ready accessibility of the compounds of this invention make them particularly promising for applications in veterinary medicine. In particular, their luteolytic properties make them useful as agents for estrus synchronization in cattle, horses and other farm animals.

METHODS

Two general methods are employed for the preparation of those compounds of formula I where R is carboxy, $R^1$ is acetyl or propionyl and $R^2$ is hydrogen, all other symbols being defined as before.

Method A

This method is used for preparation of compounds of formula II:

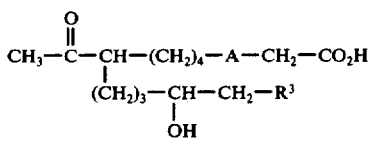

where A and $R^3$ are as defined previously.

1. Tert-butyl acetoacetate is converted to its anion by means of a strong base (sodium hydride, potassium tert-butoxide, etc.) in a solvent such as dimethylformamide (DMF) or DMF-benzene, and then alkylated with halide III

where $R^7$ = straight chain lower alkyl preferably methyl or ethyl and X = halogen (chloro, bromo or iodo) an A is as defined. The product is IV.

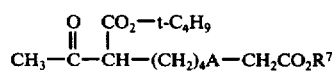

2. Compound IV is converted to its anion in like manner and alkylated with the halo-olefin V

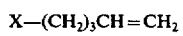

where X = halogen (chloro, bromo or iodo) to give the product VI:

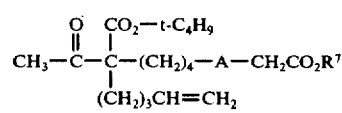

3. Compound VI is heated preferably in an inert aprotic solvent (benzene, toluene) with a trace of strong acid (sulfuric, p-toluenesulfonic acid) to effect elimination of isobutylene and decarboxylation and produce compound VII:

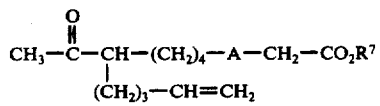

4. Compound VII is converted to the epoxide VIII by treatment with a suitable peroxide compound (peracetic acid, m-chloroperbenzoic acid) in an inert solvent (methylene chloride) at temperatures 0°–35°. The epoxide obtained is VIII:

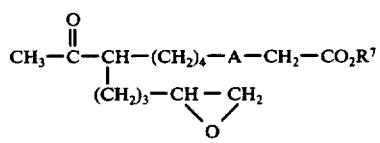

5. Epoxide VIII is treated in a solvent or solvent system such as DMF, DMF-benzene, tetrahydrofuran and the like with the anion derived from alcohol, phenol, mercaptan or thiophenol $R^6$—OH or $R^6$SH. Such anion is of course obtained by addition of suitable base (sodium hydride, potassium t-butoxide, etc.) to a solution of $R^6$—OH or $R^6$SH in above solvent system. Attack of $R^6O^-$ or $R^6S^-$ on VIII yields compound X:

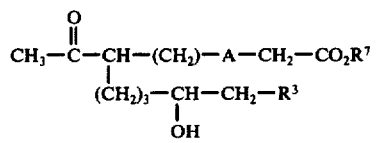

Note compound X is a product of this invention (R = COOAlk.

6. The ester X is hydrolyzed in dilute aqueous alkaline solution (preferably sodium or potassium hydroxide in aqueous methanol or ethanol) at temperatures 25°–70° to give the product of the invention II:

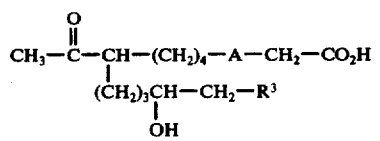

Steps 5 and 6 can be telescoped in a process where epoxide VIII is treated in an aqueous system (tetrahydrofuran-water, aqueous dimethyl sulfoxide, etc.) with sodium or potassium hydroxide and $R^6$—OH or $R^6$SH. Epoxide opening and ester hydrolysis occur simultaneously to yield product II.

Method B

This method is used for preparation of compounds of formula XI:

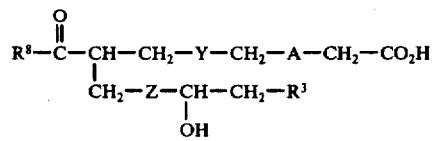

where $R^8$ is methyl or ethyl and A, Y, Z and $R^3$ are as defined previously. The method consists of the following steps:

1. A straight chain lower alkyl ester (methyl or ethyl preferably) of acetoacetic or propionylacetic acid

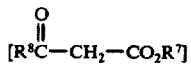

is converted to its anion with strong base (sodium hydride, potassium t-butoxide) in suitable solvent (DMF, DMF-benzene) and then alkylated with halide XII:

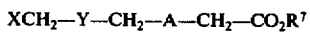

(all as previously defined)

XII to give intermediate XIII:

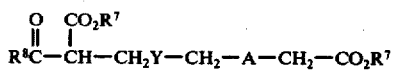

XIII

2. Intermediate XIII is converted to its anion as above and alkylated with halide XIV

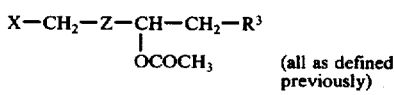   XIV (all as defined previously)

to give the interemediate ester XV

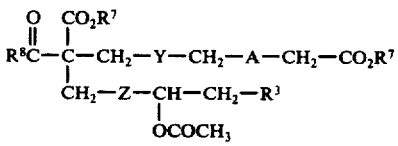

XV

3. Ester XV is treated with dilute aqueous base with addition of suitable solvent (sodium or potassium hydroxide in aqueous methanol or ethanol) at temperatures of 25°-70° for 12-24 hours to effect ester hydrolysis and decarboxylation and yield the products of the invention XI.

Further Products of the Invention

The products II and XI can be further treated to obtain other products of the invention. 1. The products II and XI can be converted to products of formula I where $R^1$ is 1-hydroxyethyl or 1-hydroxypropyl by reduction with sodium or potassium borohydride in dilute aqueous base, temperatures 25°-60°. Products II thus yield:

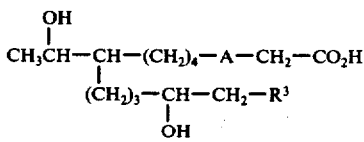

Products XI yield:

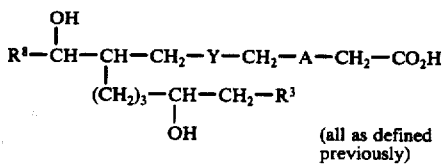

(all as defined previously)

2. The fundamental processes yield compounds where R is carboxy. To obtain carboxy salts the acid products are dissolved in a solvent such as ethanol, methanol, glyme and the like and the solution treated with an appropriate alkali or alkaline earth hydroxide or alkoxide to yield the metal salt, or with an equivalent quantity of ammonia, amine or quaternary ammonium hydroxide to yield the amine salt. In each instance, the salt either separates from the solution and may be separated by filtration or, when the salt is soluble it may be recovered by evaporation of the solvent. Aqueous solutions of the carboxylic acid salts can be prepared by treating an aqueous suspension of the carboxylic acid with an equivalent amount of an alkaline earth hydroxide or oxide, alkali metal hydroxide, carbonate or bicarbonate, ammonia, an amine or a quaternary ammonium hydroxide.

To obtain carboxy esters (i.e., compounds where R is COOAlk) the acid products are treated in ether with an ethereal solution of the appropriate diazoalkane. For example, methyl esters are produced by reaction of the acid products with diazomethane. To obtain products where R is carbamoyl, substituted carbamoyl or carbazoyl the acid product is first converted to an active Woodward ester. For example, the acid product can be made to react with N-tert-butyl-5-methylisoxazolium perchlorate in acetonitrile in the presence of a base such as triethylamine to yield an active ester in which R is

Active esters of this type can be reacted with ammonia to yield products of formula I where R is carbamoyl, with primary or secondary amines of di-lower-alkylaminoalkylamines to yield products where R is substituted carbamoyl, i.e., —CONR$^4$R$^5$, and with hydrazine to yield products where R is carbazoyl.

3. The fundamental processes yield products where $R^2$ is hydrogen. In compounds containing no additional hydroxy group and in which $R^2$ is hydrogen, reaction with formic acid, acetic anhydride, propionic anhydride, butyric anhydride, isobutyric anhydride, valeric anhydride, pivalic anhydride and the like, without solvent and at temperatures from 25° to 60° C., gives compounds wherein $R^2$ is formyl, acetyl, propionyl, butyryl, isobutyryl, valeryl, and pivaloyl, respectively.

4. Compounds where Y is cis-vinylene can be prepared from products of the invention where Y is ethynylene by hydrogenation in the presence of the Lindlar catalyst.

Preparation of Intermediates

1. Methods for the preparation of the halides III, V and XII have been described in the literature. 2. Varied methods are used for the preparation of the halides XIV.

a. When Z is ethynylene these intermediates can be represented by formula XIVa

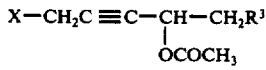

The preparation of XIVa is as follows:

Phenol, thiophenol, alcohol or mercaptan, $R^6OH$ or $R^6SH$, is treated with base (sodium hydride, potassium-t-butoxide, etc.) in suitable solvent (DMF, t-butanol) and then made to react with bromoacetaldehyde diethyl (or dimethyl) acetal to give $R^3CH_2CH(OC_2H_5)_2$. This acetal is hydrolyzed in aqueous acidic medium preferably at 80°–120° to give the substituted acetaldehyde $R^3CH_2CHO$. The acetaldehyde is treated with the acetylenic Grignard reagent prepared from tetrahydro-2-(2-propynyloxy)-2H-pyran (THP—$OCH_2C\equiv CH$, where THP = 2-tetrahydropyranyloxy) to give after workup the acetylenic alcohol THP—O—$CH_2C\equiv C$—CHOH—$CH_2$—$R^3$. This alcohol is acetylated preferably with acetic anhydride in pyridine to yield THP—O—$CH_2C\equiv C$—CH(OCOCH$_3$)—$CH_2$—$R^3$. The tetrahydropyranyl protecting group is hydrolyzed in aqueous acidic medium to yield primary acetylenic alcohol $HOCH_2C\equiv C$—CH(OCOCH$_3$)$CH_2R^3$. Treatment of this alcohol with phosphorus tribromide in ether at 10°–35° yields $BrCH_2C\equiv C$—CH(OCOCH$_3$)$CH_2$—$R^3$, a compound of formula XIVa where X = Br.

b. When Z is trans-ethylene, the intermediates XIV can be represented by formula XIVb

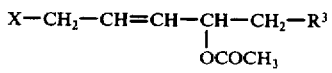

The preparation of XIVb begins with the protected acetylenic alcohol, $THPOCH_2C\equiv C$—CHOH—$CH_2$—$R^3$, used in the preparation of XIVa. In this case, the acetylenic alcohol is reduced with lithium aluminum hydride in a suitable solvent such as ether or tetrahydrofuran to give the trans olefinic alcohol THP—O—$CH_2CH=CH$—CHOH—$CH_2$—$R^3$. The alcohol is acetylated preferably with acetic anhydride in pyridine to yield THP—O—$CH_2$—CH=CH—CH(OCOCH$_3$)—$CH_2$—$R^3$. The tetrahydropyranyl group is hydrolyzed in aqueous acidic medium to yield $HOCH_2CH=CH$—CH(OCOCH$_3$)—$CH_2R^3$. This alcohol can be converted to the halide XIVb by a variety of procedures. For example, the alcohol on treatment with phosphorus tribromide in ether gives XIVb where X is bromo. Or, the alcohol can be treated with p-toluenesulfonyl chloride in pyridine to obtain the tosylate which can be made to react with sodium iodide in acetone to yield XIVb where X is iodo.

c. When Z is ethylene, the intermediate XIV can be represented by formula XIVc

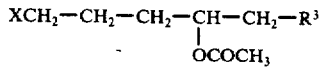

The preparation of XIVc begins with the protected acetylenic acetate, THP—O—$CH_2C\equiv C$—CH(OCOCH$_3$)—$CH_2$—$R^3$, used in the preparation of XIVa. Here, this compound is hydrogenated preferably over a palladium catalyst in an aprotic solvent at 1–4 atmospheres and 20°–40°. The saturated compound THP—O—$(CH_2)_3$—CH(OCOCH$_3$)—$CH_2R^3$ is obtained. The tetrahydropyranyl group is hydrolyzed in aqueous acidic medium to give HO—$(CH_2)_3$—CH(OCOCH$_3$)—$CH_2$—$R^3$. This alcohol is treated with p-toluenesulfonyl chloride in pyridine to yield the tosylate which when treated with sodium iodide in acetone undergoes metathesis to yield I—$(CH_2)_3$—CH(OCOCH$_3$)—$CH_2$—$R^3$ which is a compound of formula XIVc where X = iodo.

EXAMPLE 1

Preparation of 8-Acetyl-12-hydroxy-13-(4-fluorophenoxy)tridecanoic Acid

Step A: Preparation of Ethyl 8-Tert-butoxycarbonyl-9-oxodecanoate

A suspension of 57% sodium hydride in mineral oil (21.1 g. net wt.; 0.88 mole) in a solvent mixture of benzene (400 ml.) and dimethylformamide (400 ml.) is treated, dropwise, over 30 minutes with tert-butyl acetoacetate (126.56 g.; 0.80 mole). Stirring is continued for an additional 30 minutes. Then ethyl 7-bromoheptanoate (208.50 g.; 0.88 mole) is added, dropwise, over 30 minutes and the mixture is heated at 100° C. for 2½ hours.

The cooled reaction mixture is treated with water (1600 ml.) and the organic layer is separated. The aqueous layer is extracted with ether. The combined organic solutions are washed with saturated sodium chloride solution and then dried over anhydrous sodium sulfate. The solvents are removed under vacuum and the residual oil is distilled to give 158.6 g. (63%) of yellow oil, b.p. 175°–177°/0.5 mm.

Step B. Preparation of Ethyl 8-Acetyl-8-tert-butoxycarbonyl-12-tridecenoate

A suspension of 57% sodium hydride in mineral oil (2.7 g. net wt.; 0.113 mole) in a solvent mixture of benzene (50 ml.) and dimethylformamide (50 ml.) is treated, dropwise, over 30 minutes with ethyl 8-tert-butoxycarbonyl-9-oxodecanoate (32.35 g.; 0.103 mole). Stirring is continued for an additional 30 minutes. Then 5-bromo-1-pentene (16.84 g.; 0.113 mole) is added, dropwise, over 15 minutes. A trace of sodium iodide is added and the mixture is heated at 100° for 20 hours.

The cooled reaction mixture is treated with water (200 ml.) and the organic layer is separated. The aqueous layer is extracted with ether. The combined organic solutions are washed with saturated sodium chloride solution and then dried over anhydrous sodium sulfate. The solvents are removed under vacuum to give the title compound as a residual oil. The yield is 39.40 g.; pmr (CDCl$_3$) δ 1.47 [9H, s (CH$_3$)$_3$C], 2.10 (3H, s CH$_3$CO), 4.17 (2H, q CH$_2$O), 4.90–5.12 (2H, m CH$_2$=), 5.40–6.07 (1H, m CH=).

Step C. Preparation of Ethyl 8-Acetyl-12-tridecenoate

A mixture of ethyl 8-acetyl-8-tert-butoxycarbonyl-12-tridecenoate (39.40 g.; 0.103 mole), p-toluenesulfonic acid monohydrate (1.76 g.), toluene (176 ml.) and acetic anhydride (2 ml.) is heated under reflux for 23½ hours.

The cooled reaction mixture is washed with saturated sodium bicarbonate solution, then saturated sodium chloride solution and dried over anhydrous sodium sulfate. The solvent is removed under vacuum and the residual oil is distilled to give 15.26 g. (53%) of colorless oil, b.p. 135°–137°/0.1 mm; pmr (CDCl$_3$) δ 2.07 (3H, s CH$_3$CO), 4.10 (2H, q CH$_2$O), 4.90–5.12 (2H, m CH$_2$=), 5.40–6.07 (1H, m CH=).

Step D. Preparation of Ethyl 8-Acetyl-12,13-epoxytridecanoate

A solution of ethyl 8-acetyl-12-tridecenoate (68.30 g.; 0.242 mole) in methylene chloride (500 ml.) is treated with a solution of m-chloroperbenzoic acid (45.90 g.; 0.266 mole) in methylene chloride (500 ml.). The colorless solution is stirred at room temperature for 7 hours.

The reaction mixture is treated with 5% aqueous sodium hydroxide solution until the aqueous phase remains strongly alkaline. The organic layer is separated, washed well with saturated sodium chloride solution and then dried over anhydrous sodium sulfate. The solvent is removed under vacuum to give the title compound as a residual oil. The yield is 72.21 g.; pmr (CDCl$_3$) δ 2.10 (3H, s CH$_3$CO), 4.15 (2H, q CH$_2$O).

Step E. Preparation of Ethyl 8-Acetyl-12-hydroxy-13-(4-fluorophenoxy)tridecanoate A suspension of 57% sodium hydride in mineral oil (0.7 g. net wt.; 0.0292 mole in a solvent mixture of benzene (15 ml.) and dimethylformamide (15 ml.) is treated, dropwise, over 15 minutes with a solution of 4-fluorophenol (3.27 g.; 0.0292 mole) in a solvent mixture of benzene (5 ml.) and dimethylformamide (5 ml.). Stirring is continued for an additional 15 minutes. Then a solution of ethyl 8-acetyl-12,13-epoxytridecanoate (7.90 g.; 0.0265 mole) in a solvent mixture of benzene (10 ml.) and dimethylformamide (10 ml.) is added, dropwise, over 15 minutes and the mixture is heated at 90° for 19 hours.

The cooled reaction mixture is treated with water (120 ml.) and the organic layer is separated. The aqueous layer is extracted with ether. The combined organic solutions are washed with saturated sodium bicarbonate solution, then saturated sodium chloride solution and dried over anhydrous sodium sulfate. The solvents are removed under vacuum to give the title compound as a residual oil. The oil is purified by column chromatography on silica gel with 1% methanol in chloroform as an eluant, pmr (CDCl$_3$) δ 2.13 (3H, s CH$_3$CO), 6.95 (4H, m aryl H).

Step F. Preparation of 8-Acetyl-12-hydroxy-13-(4-fluorophenoxy)tridecanoic Acid Ethyl 8-Acetyl-12-hydroxy-13-(4-fluorophenoxy)tridecanoate (4.67 g.; 0.0113 mole) is added to a solution of sodium hydroxide (0.68 g.; 0.0170 mole) in water (6.3 ml.) and methanol (56.7 ml.). The resulting solution is allowed to stand for 69 hours at 25°.

Most of the methanol is then removed under vacuum. The residue is diluted with water (55 ml.) and extracted with ether. The aqueous layer is acidified with concentrated hydrochloric acid to the Congo Red endpoint. The product precipitates as an oil. It is purified by column chromatography on silica gel with 2% methanol in chloroform as eluant, pmr (CDCl$_3$) δ 2.10 (3H, s CH$_3$CO), 3.95 (3H, s CH$_2$O + CHO) 6.30 (2H, broad s OH, COOH), 6.83 (4H, m aryl H).

Anal. calc'd. for C$_{21}$H$_{31}$FO$_5$: C, 65.95; H, 8.17; Found: C, 66.25; H, 8.38

EXAMPLE 2

Preparation of 8-(1-Hydroxyethyl)-12-hydroxy-13-(4-fluorophenoxy)-tridecanoic Acid Sodium borohydride (1.2 g., 0.03 mole) is added to a solution of 8-acetyl-12-hydroxy-13-(4-fluorophenoxy)-tridecanoic acid (15.4 g., 0.04 mole) and sodium hydroxide (2.0 g., 0.05 mole) in 70 ml. of water. The resulting solution is allowed to stand at room temperature for 19 hours, and is then acidified to Congo Red with concentrated hydrochloric acid. The oily product is taken up in ether, washed with water and dried over sodium sulfate. The ether is evaporated leaving 12.8 g. of the crude title compound as a brown oil.

The product is purified by chromatography on a column containing 250 g. of silica gel made up in chloroform. The column is eluted with 2% methanol in chloroform and finally with 4% methanol in chloroform. Fractions are combined and evaporated to yield a product with Rf 0.19 on silica gel thin layer plates with an eluant of chloroform-methanol-acetic acid, 95:4:1. The purified product weighs 2.6 g. and is an orange viscous oil; pmr (CDCl$_3$) δ 2.33 (2H, t, CH$_2$CO$_2$H); δ 3.8–4.2 (4H, m CH$_2$O and CHO); 5.55 (3H, s OH and CO$_2$H); 6.95 (4H, m aryl H)

Anal. Calc'd. for C$_{21}$H$_{33}$FO$_5$: C, 65.60; H, 8.65; Found: C, 65.91; H, 8.88

EXAMPLE 3

Preparation of 5-Acetyl-9-hydroxy-10-(4-fluorophenoxy)-decyloxyacetic Acid

The synthesis of this compound is carried out by the procedures described in Example 1 except that, in Step A, an equivalent amount of ethyl 4-iodobutoxyacetate is substituted for ethyl 7-bromoheptanoate. Thus, there are obtained successively:

ethyl 5-tert-butoxycarbonyl-6-oxoheptyloxyacetate (Step A);
ethyl 5-acetyl-5-tert-butoxycarbonyl-9-decenyloxyacetate (Step B);
ethyl 5-acetyl-9-decenyloxyacetate (Step C);
ethyl 5-acetyl-9,10-epoxydecyloxyacetate (Step D);
ethyl 5-acetyl-9-hydroxy-10-(4-fluorophenoxy)-decyloxyacetate (Step E); and
5-acetyl-9-hydroxy-10-(4-fluorophenoxy)-decyloxyacetic acid (Step F).

EXAMPLE 4

Preparation of 8-Acetyl-12-hydroxy-13-(4-fluorophenoxy)-5-tridecynoic Acid

Step A. Preparation of Methyl 8-Ethoxycarbonyl-9-oxo-5-decynoate

A suspension of 57% sodium hydride in mineral oil (4.37 g. net wt.; 0.182 mole) in a solvent mixture of benzene (82.5 ml.) and dimethylformamide (82.5 ml.) is treated, dropwise, over 30 minutes with ethyl acetoacetate (21.47 g.; 0.165 mole). Stirring is continued for an additional 30 minutes. Then methyl 7-bromo-5-heptynoate (39.87 g.; 0.182 mole) is added, dropwise, over 30 minutes. The mixture is stirred at room temperature for 1 hour, then heated to 70° and maintained at 70° for 1 hour.

The cooled reaction mixture is treated with water (330 ml.) and the organic layer is separated. The aqueous layer is extracted with ether. The combined organic solutions are washed with saturated sodium chloride solution and then dried over anhydrous sodium sulfate. The solvents are removed under vacuum and the residue distilled to obtain 22.0 g. of product, b.p. 140°–142°/0.1 mm.

Anal. Calc'd. for $C_{14}H_{20}O_5$: C, 62.67; H, 7.51. Found: C, 62.45; H, 7.74.

Step B-1. Preparation of 4-Fluorophenoxyacetaldehyde Diethyl Acetal

A solution of p-fluorophenol (28.1 g., 0.25 mole) in DMF (30 ml.) is added dropwise to a suspension of hexane (2 × 30 ml.)-prewashed sodium hydride (50% oil dispersion, 12.5 g., 0.26 mole) in DMF (120 ml.). The resulting mixture is stirred at room temperature for 10 minutes, treated with bromoacetaldehyde diethyl acetal (49.3 g., 0.25 mole) and finally heated on a steam bath for 4 hours. The reaction mixture is allowed to come to room temperature and the precipitated sodium bromide is filtered off. DMF is then removed on a rotary evaporator, the oil residue is diluted with acetone (100 ml.) and another quantity of sodium bromide is precipitated which again is removed by filtration. The filtrate is then concentrated on a rotary evaporator leaving an oil residue which is vacuum distilled at 87°/0.05 mm to yield the desired product as colorless oil (46.7 g., 0.205 mole, 82%). Ir (neat) 3.4~3.5, 6.21, 6.64, 8.00, 8.25, 8.83, 9.32, 12.08, 13.20μ; pmr (CCl₄) δ 1.17 (6H, t J=7.5Hz), 3.57 (2H, q, J=7.5 Hz), 3.61 (2H, q, J=7.5 Hz), 3.85 (2H, d, J=5Hz), 4.68 (1H, t, J=5Hz), 6.6–7.1 (4H, m).

Step B-2. Preparation of 4-Fluorophenoxyacetaldehyde

A mixture of 4-fluorophenoxyacetaldehyde diethyl acetal (30.0 g., 0.131 mole) acetone (150 ml.), water (150 ml.), and concentrated sulfuric acid (0.8 ml.) is refluxed overnight (ca. 16 hours). The mixture is allowed to cool to room temperature, and is then extracted with methylenechloride four times. The combined extracts are washed with aqueous sodium bicarbonate and dried over anhydrous magnesium sulfate. The solvent is stripped off on a rotary evaporator and the oil residue is subsequently distilled in vacuo at 70°/0.05 mm to give the title compound (19.0 g., 0.123 mole, 94%). ir (neat) 3.23, 3.50, 3.63, 5.71, 6.62, 7.00, 8.00, 8.24, 9.07, 9.38, 12.03, 12.51, 13.12μ; pmr (CCl₄) δ 4.37 (2H, d, J=1Hz), 6.6–7.1 (4H, m), 9.68 (1H, t, J=1Hz).

Step B-3. Preparation of 1-(2-Tetrahydropyranyloxy)-4-acetoxy-5-(4-fluorophenoxy)-2-pentyne To the Grignard reagent prepared from magnesium (11.58 g.; 0.476 mole) and bromoethane (51.88 g.; 0.476 mole) in tetrahydrofuran (400 ml.) is added, dropwise, during 30 minutes, a solution of tetrahydro-2-(2-propynyloxy)-2H-pyran (64.06 g.; 0.457 mole) in tetrahydrofuran (40 ml.). The mixture is stirred at room temperature, under nitrogen, for 1 hour, then chilled in an ice bath and treated, dropwise, during 30 minutes, with a solution of 4-fluorophenoxyacetaldehyde (61.20 g.; 0.397 mole) in tetrahydrofuran (60 ml.). The mixture is heated on a steam bath, under nitrogen, for 1 hour, then again chilled in an ice bath and treated, dropwise, during 30 minutes, with a mixture of acetic anhydride (48.60 g.; 0.476 mole) and pyridine (75.31 g.; 0.952 mole). The mixture is heated on a steam bath, under nitrogen, for 30 minutes.

The mixture is poured into cold water (1200 ml.) and the organic layer is separated. The aqueous layer is extracted with ether. The combined organic extracts are washed with water and then dried over anhydrous magnesium sulfate. The solvent is removed under vacuum to give the title compound as an orange-red residual oil, yield 133.54 g.; pmr (CDCl₃) δ 2.07 (3H, s CH₃COO), 4.17 (2H, d CH₂O), 4.32 (2H, d CH₂C≡C), 5.78 (1H, m CHOCO), 6.95 (4H, m aryl H).

Step B-4. Preparation of 1-(2-Tetrahydropyranyloxy)-4-acetoxy-5-(4-fluorophenoxy) pentane 1-(2-Tetrahydropyranyloxy)-4-acetoxy-5-(4-fluorophenoxy)-2-pentyne (13.4 g.; 0.04 mole) is dissolved in ethyl acetate (100 ml.). 5% Palladium on carbon is added and the mixture is hydrogenated on the Parr apparatus at an initial pressure of 41 lbs./in² and 25°. When 0.08 mole of hydrogen is absorbed, the catalyst is removed by filtration and the solvent is evaporated under vacuum to give the title compound as a light orange residual oil, yield 12.90 g.

Step B-5. Preparation of 4-Acetoxy-5-(4-fluorophenoxy)-1-pentanol

A mixture of 1-(2-tetrahydropyranyloxy)-4-acetoxy-5-(4-fluorophenoxy)-pentane (143.5 g., 0.422 mole), methanol (700 ml.), concentrated hydrochloric acid (3 ml.) and ethyl acetate (70 ml.) is stirred at room temperature for 1 hour.

The reaction mixture is poured into cold H₂O (1500 ml.) and the organic layer is extracted with ether. The combined extracts are washed with saturated sodium bicarbonate solution, then brine and dried over anhydrous magnesium sulfate. The solvent is removed under vacuum and the residual oil is distilled to give the title compound as a light yellow oil, yield 72.6 g. (67%), b.p. 158°–160°/0.1 mm; pmr (CDCl₃) δ 2.08 (3H, s CH₃COO), 3.65 (2H, t HOCH₂), 4.00 (2H, d CH₂O), 5.18 (1H, m CHOCO), 6.83 (4H, m aryl H).

Step B-6. Preparation of 4-Acetoxy-5-(4-fluorophenoxy)-1-pentanol Tosylate

A solution of p-toluenesulfonyl chloride (42.0 g., 0.22 mole) in pyridine (100 ml.) is cooled in an ice bath while 4-acetoxy-5-(4-fluorophenoxy)-1-pentanol (49.7 g., 0.193 mole) is added dropwise with stirring during 40 minutes. The ice bath is replaced by a cool (20°) water bath and stirred is continued for 2 hours. The mixture is then poured into 500 ml. of water. The oily product is taken up in ether, washed with 2N hydrochloric acid and water and dried over sodium sulfate. The solvent is distilled in vacuo to leave 73.5 g. (93%) of the crude title compound as a yellow oil.

Step B-7. Preparation of 4-Acetoxy-5-(4-fluorophenoxy)-1-iodopentane

A solution of 4-acetoxy-5-(4-fluorophenoxy)-1-pentanol tosylate (73.5 g., 0.179 mole) and sodium iodide (79.5 g., 0.53 mole) in acetone (500 ml.) is allowed to stand at 25°–27° for 18 hours. The precipitated sodium tosylate is filtered off. Most of the acetone is evaporated from the filtrate and the residue is treated with 300 ml. of water. The oily product is taken up in ether, washed with dilute sodium thiosulfate solution, water and brine and dried over sodium sulfate. The solvent is distilled in vacuo to give 66 g. (a quantitative yield) of the crude title compound as a yellowish oil which is used without further purification; pmr (CDCl$_3$) δ 2.05 (3H, s CH$_3$CO); 3.20 (2H, t CH$_2$I); 3.97 (2H, d CH$_2$O); 5.20 (1H, m CHO); 6.85 (4H, m aryl).

Step C. Preparation of Methyl 8-Acetyl-8-ethoxycarbonyl-12-acetoxy-13-(4-fluorophenoxy)-5-tridecynoate A suspension of 57% sodium hydride in mineral oil (4.15 g. net wt.; 0.173 mole) in a solvent mixture of benzene (82.5 ml.) and dimethylformamide (82.5 ml.) is treated, dropwise, over 30 minutes with methyl 8-ethoxycarbonyl-9-oxo-5-decynoate (44.27 g.; 0.165 mole). Stirring is continued for an additional 30 minutes. Then 4-acetoxy-5-(4-fluorophenoxy)-1-iodopentane (65.60 g.; 0.179 mole) is added, dropwise, over 15 minutes. Stirring is continued for an additional 30 minutes. The mixture is then heated to 60° and maintained at 60° for 3½ hours.

The cooled reaction mixture is treated with water (330 ml.) and the organic layer is separated. The aqueous layer is extracted with ether. The combined organic solutions are washed with saturated sodium chloride solution and then dried over anhydrous sodium sulfate. The solvents are removed under vacuum to give the title compound as a residual oil. The yield is 83.59 g.; pmr (CDCl$_3$) δ 2.05 (3H, s CH$_3$COO), 2.13 (3H, s CH$_3$CO), 3.65 (3H, s CH$_3$O), 3.95 (2H, d CH$_2$O), 5.19 (1H, m CHOCO), 6.78 (4H, m aryl H).

Step D. Preparation of 8-Acetyl-12-hydroxy-13-(4-fluorophenoxy)-5-tridecynoic Acid Methyl 8-acetyl-8-ethoxycarbonyl-12-acetoxy-13-(4-fluorophenoxy)-5-tridecynoate (40.00 g., 0.079 mole) is added to a solution of sodium hydroxide (18.96 g.; 0.474 mole) in water (132.7 ml.) and methanol (462.9 ml.). The resulting solution is allowed to stand for 19½ hours at 55°.

Most of the methanol is then removed under vacuum. The residue is diluted with water (320 ml.) and extracted with ether. The aqueous layer is acidified with concentrated hydrochloric acid to the Congo Red endpoint. The product precipitates as an oil. It is purified by column chromatography on silica gel with 2% methanol in chloroform as eluant, pmr (CDCl$_3$) δ 2.18 (3H, s CH$_3$CO), 3.93 (2H, d CH$_2$O), 7.0 (4H, m aryl H), 8.08 (2H, broad s OH, COOH).

Following the procedure of Example 4, Step B-1 but substituting for the p-fluorophenol used therein an equivalent amount of
1. 3-fluorophenol
2. 3-bromophenol
3. 3-iodophenol
4. 3-chlorophenol
5. 3-methylphenol
6. 3-mesylphenol
7. 3-dimethylaminophenol
8. 3-methoxyphenol
9. 3-ethylphenol
10. 3-ethoxyphenol
11. 2,3-difluorophenol
12. 3,4-methylenedioxyphenol
13. 2,4-dichlorophenol
14. 3-trifluoromethylphenol, respectively, and conducting the reaction and isolating the product as described in Step A and using the product in each of Steps B-2 through D, there is obtained
1. 8-acetyl-12-hydroxy-13-(3-fluorophenoxy)-5-tridecynoic acid
2. 8-acetyl-12-hydroxy-13-(3-bromophenoxy)-5-tridecynoic acid
3. 8-acetyl-12-hydroxy-13-(3-iodophenoxy)-5-tridecynoic acid
4. 8-acetyl-12-hydroxy-13-(3-chlorophenoxy)-5-tridecynoic acid
5. 8-acetyl-12-hydroxy-13-(3-methylphenoxy)-5-tridecynoic acid
6. 8-acetyl-12-hydroxy-13-(3-mesylphenoxy)-5-tridecynoic acid
7. 8-acetyl-12-hydroxy-13-(3-dimethylaminophenoxy)-5-tridecynoic acid
8. 8-acetyl-12-hydroxy-13-(3-methoxyphenoxy)-5-tridecynoic acid
9. 8-acetyl-12-hydroxy-13-(3-ethylphenoxy)-5-tridecynoic acid
10. 8-acetyl-12-hydroxy-13-(3-ethoxyphenoxy)-5-tridecynoic acid
11. 8-acetyl-12-hydroxy-13-(2,3-difluorophenoxy)-5-tridecynoic acid
12. 8-acetyl-12-hydroxy-13-(3,4-methylenedioxyphenoxy)-5-tridecynoic acid
13. 8-acetyl-12-hydroxy-13-(2,4-dichlorophenoxy)-5-tridecynoic acid
14. 8-acetyl-12-hydroxy-13-(3-trifluoromethylphenoxy)-5-tridecynoic acid, respectively.

EXAMPLE 5

Preparation of 8-Acetyl-12-hydroxy-13-(4-fluorophenoxy)-5-cis-tridecenoic Acid 8-Acetyl-12-hydroxy-13-(4-fluorophenoxy)-5-tridecynoic acid (10.8 g., 0.287 mole) is dissolved in ethyl acetate (90 ml.) and hydrogenated over Lindlar catalyst (1.5 g.) at atmospheric pressure and room temperature. One molar equivalent of hydrogen is absorbed in 90 minutes whereupon uptake of hydrogen ceases. The catalyst is filtered off and the solvent evaporated to leave the product as a residual oil. Purification is effected by chromatography on a column containing 180 g. of silica gel with 2% methanol in chloroform as eluant. The purified product is a nearly colorless viscous oil with Rf 0.43 on silica gel thin layer plates developed with chloroform-methanol-acetic acid 95:4:1; pmr (CDCl$_3$) δ 2.12 (3H, s CH$_3$CO), 3.91 (3H, m CHO, CH$_2$O), 5.40 (2H, m vinyl CH), 7.0 (4H, m aryl H).

Following the procedure of Example 5, but substituting for the 8-acetyl-12-hydroxy-13-(4-fluorophenoxy)-5-tridecynoic acid, each of the 14 products listed in Example 4, conducting the reaction and isolating the product as described in Example 5, there is obtained:
1. 8-acetyl-12-hydroxy-13-(3-fluorophenoxy)-5-cis-tridecenoic acid
2. 8-acetyl-12-hydroxy-13-(3-bromophenoxy)-5-cis-tridecenoic acid
3. 8-acetyl-12-hydroxy-13-(3-iodophenoxy)-5-cis-tridecenoic acid
4. 8-acetyl-12-hydroxy-13-(3-chlorophenoxy)-5-cis-tridecenoic acid
5. 8-acetyl-12-hydroxy-13-(3-methylphenoxy)-5-cis-tridecenoic acid 6. 8-acetyl-12-hydroxy-13-(3-mesylphenoxy)-5-cis-tridecenoic acid
7. 8-acetyl-12-hydroxy-13-(3-dimethylaminophenoxy)-5-cis-tridecenoic acid
8. 8-acetyl-12-hydroxy-13-(3-methoxyphenoxy)-5-cis-tridecenoic acid
9. 8-acetyl-12-hydroxy-13-(3-ethylphenoxy)-5-cis-tridecenoic acid
10. 8-acetyl-12-hydroxy-13-(3-ethoxyphenoxy)-5-cis-tridecenoic acid
11. 8-acetyl-12-hydroxy-13-(2,3-difluorophenoxy)-5-cis-tridecenoic acid
12. 8-acetyl-12-hydroxy-13-(3,4-methylenedioxyphenoxy)-5-cis-tridecenoic acid
13. 8-acetyl-12-hydroxy-13-(2,4-dichlorophenoxy)-5-cis-tridecenoic acid
14. 8-acetyl-12-hydroxy-13-(3-trifluoromethylphenoxy)-5-cis-tridecenoic acid, respectively.

EXAMPLE 6

Preparation of 8-(1-Hydroxyethyl)-12-hydroxy-13-(4-fluorophenoxy)-5-cis-tridecenoic Acid The synthesis of this compound is carried out by the method described in Example 2 except that an equivalent quantity of 8-acetyl-12-hydroxy-13-(4-fluorophenoxy)-cis-5-tridecenoic acid is substituted for the 8-acetyl-12-hydroxy-13-(4-fluorophenoxy) tridecanoic acid of Example 2. The title compound is obtained as a viscous colorless oil.

Following the procedure of Example 6 but substituting for the 8-acetyl-12-hydroxy-13-(4-fluorophenoxy)-5-cis-tridecenoic acid an equivalent amount of the 14 products listed in Example 5, conducting the reaction and isolating the product as described in Example 6, there is obtained:

1. 8-(1-hydroxyethyl)-12-hydroxy-13-(3-fluorophenoxy)-5-cis-tridecenoic acid
2. 8-(1-hydroxyethyl)-12-hydroxy-13-(3-bromophenoxy)-5-cis-tridecenoic acid
3. 8-(1-hydroxyethyl)-12-hydroxy-13-(3-iodophenoxy)-5-cis-tridecenoic acid
4. 8-(1-hydroxyethyl)-12-hydroxy-13-(3-chlorophenoxy)-5-cis-tridecenoic acid
5. 8-(1-hydroxyethyl)-12-hydroxy-13-(3-methylphenoxy)-5-cis-tridecenoic acid
6. 8-(1-hydroxyethyl)-12-hydroxy-13-(3-mesylphenoxy)-5-cis-tridecenoic acid
7. 8-(1-hydroxyethyl)-12-hydroxy-13-(3-dimethylaminophenoxy)-5-cis-tridecenoic acid
8. 8-(1-hydroxyethyl)-12-hydroxy-13-(3-methoxyphenoxy)-5-cis-tridecenoic acid
9. 8-(1-hydroxyethyl)-12-hydroxy-13-(3-ethylphenoxy)-5-cis-tridecenoic acid
10. 8-(1-hydroxyethyl)-12-hydroxy-13-(3-ethoxyphenoxy)-5-cis-tridecenoic acid
11. 8-(1-hydroxyethyl)-12-hydroxy-13-(2,3-difluorophenoxy)-5-cis-tridecenoic acid
12. 8-(1-hydroxyethyl)-12-hydroxy-13-(3,4-methylenedioxyphenoxy)-5-cis-tridecenoic acid
13. 8-(1-hydroxyethyl)-12-hydroxy-13-(2,4-dichlorophenoxy)-5-cis-tridecenoic acid
14. 8-(1-hydroxyethyl)-12-hydroxy-13-(3-trifluoromethylphenoxy)-5-cis-tridecenoic acid, respectively.

EXAMPLE 7

Preparation of 8-Acetyl-12-hydroxy-13-(4-fluorophenoxy)-10-tridecynoic Acid

Step A. Preparation of Diethyl 2-Acetylazelate

This compound is prepared by the procedure described in Example 1, Step A, except that an equivalent amount of ethyl acetoacetate is substituted for the tert-butyl acetoacetate therein employed. Diethyl 2-acetylazelate is obtained as a light yellow oil, b.p. 155°-157°/0.05 mm.

Step B-1. Preparation of 4-Acetoxy-5-(4-fluorophenoxy)-2-pentyn-1-ol

This compound is prepared by the procedure described in Example 4, Step B-5, except that 1-(2-tetrahydropyranyloxy)-4-acetoxy-5-(4-fluorophenoxy)-2-pentyne (Example 4, Step B-3) is substituted for 1-(2-tetrahydropyranyloxy)-4-acetoxy-5-(4-fluorophenoxy)-pentane. The title compound is obtained as a light yellow oil which is not distilled but used directly in the next step.

Step B-2. Preparation of 4-Acetoxy-1-bromo-5-(4-fluorophenoxy)-2-pentyne

Phosphorus tribromide (10.6 g., 0.039 mole) is added dropwise during 15 minutes to a solution of 4-acetoxy-5-(4-fluorophenoxy)-2-pentyn-1-ol (25.1 g., 0.10 mole) in ether (80 ml.). The resulting solution is stirred at room temperature for 1 hour and then heated at reflux for 30 minutes. The solution is poured into 100 ml. of ice water. The organic layer is separated, washed with water and dried over $Na_2SO_4$. The solvent is evaporated under reduced pressure to leave the title compound as a light yellow oil.

Step C. Preparation of Ethyl 8-Acetyl-8-ethoxycarbonyl-12-acetoxy-13-(4-fluorophenoxy)-10-tridecynoate A suspension of 57% sodium hydride in mineral oil (4.8 g., net wt., 0.2 mole) in a solvent mixture of benzene (100 ml.) and dimethylformamide (100 ml.) is treated dropwise over 30 minutes with diethyl 2-acetylazelate (57.0 g., 0.2 mole). Stirring is continued for an additional 30 minutes. Then, 4-acetoxy-1-bromo-5-(4-fluorophenoxy)-2-pentyne (63.0 g., 0.2 mole) is added dropwise during 30 minutes. The mixture is then heated at 60° for 4 hours.

The cooled reaction mixture is treated with water (500 ml.) and the organic layer separated. The organic layer is diluted with ether, washed with water and brine and dried over sodium sulfate. The solvents are removed in vacuo to give the title compound as an orange viscous oil.

Step D. Preparation of 8-Acetyl-12-hydroxy-13-(4-fluorophenoxy)-10-tridecynoic Acid The synthesis of this compound is carried out by the basic hydrolytic procedure described in Example 4, Step D except that an equivalent amount of ethyl 8-acetyl-8-ethoxycarbonyl-12-acetoxy-13-(4-fluorophenoxy)-10-tridecynoate is substituted for the methyl 8-acetyl-8-ethoxycarbonyl-12-acetoxy-13-(4-fluorophenoxy)-5-tridecynoate of Example 4, Step D. The product is purified by column chromatography on silica gel and is a light yellow viscous oil.

Example 8

Preparation of 8-Acetyl-12-hydroxy-13-(4-fluorophenoxy)-5-cis-10-trans-tridecadienoic Acid

Step A-1. Preparation of 1-(2-Tetrahydropyranyloxy)-4-hydroxy-5-(4-fluorophenoxy)-2-pentyne To the Grignard reagent prepared from magnesium (12.2 g., 0.5 mole) and bromoethane (54.5 g., 0.5 mole) in tetrahydrofuran (400 ml.) is added, dropwise, during 30 minutes, a solution of tetrahydro-2-(2-propynyloxy)-2H-pyran (67.3 g., 0.5 mole) in tetrahydrofuran (50 ml.). The mixture is stirred at room temperature for 1 hour and then treated, dropwise, during 1 hour with 4-fluorophenoxy-acetaldehyde (61.6 g., 0.4 mole). The resulting mixture is heated at reflux for 1 hour, then cooled and poured into an ice cold saturated solution of ammonium chloride in water.

The organic layer is separated, diluted with ether, washed with water and brine, and dried over magnesium sulfate. The solvents are removed under vacuum to give the title compound as a yellow residual oil.

Step A-2. Preparation of 1-(2-Tetrahydropyranyloxy)-4-hydroxy-5-(4-fluorophenoxy)-trans-2-pentene Lithium aluminum hydride (7.6 g., 0.2 mole) is dissolved in ether (225 ml.) and 1-(2-tetrahydropyranyloxy)-4-hydroxy-5-(4-fluorophenoxy)-2-pentyne (35.2 g., 0.12 mole) is added dropwise with stirring during 1.5 hour. The resulting mixture is stirred at 25° for 21 hours and then heated at reflux for 4 hours. The mixture is cooled and treated dropwise with ethyl acetate to consume excess lithium aluminum hydride. It is then poured into 600 ml. of ice-cold 20% aqueous potassium hydroxide solution. The oily product is taken up in ether, washed with water and brine, and dried over magnesium sulfate. Removal of solvent under vacuum leaves the title compound as a yellow residual oil.

Step A-3. Preparation of 1-(2-Tetrahydropyranyloxy)-4-acetoxy-5-(4-fluorophenoxy)-trans-2-pentene A mixture of 1-(2-tetrahydropyranyloxy)-4-hydroxy-5-(4-fluorophenoxy)-trans-2-pentene (23.6 g., 0.08 mole), acetic anhydride (9.2 g., 0.09 mole), and pyridine (7.9 g., 0.1 mole) is heated at 55°-60° for 4 hours and then at 95° for an additional 4 hours. The solution is cooled, diluted with ether and washed with ice-cold saturated sodium carbonate solution, ice water (3 x) and brine, and dried over sodium sulfate. Removal of solvent under vacuum leaves the title compound as a residual orange oil.

Step A-4. Preparation of 4-Acetoxy-5-(4-fluorophenoxy)-trans-2-penten-1-ol

The synthesis of this compound is carried out by the procedure of Example 4, Step B-5 except that an equivalent quantity of 1-(2-tetrahydropyranyloxy)-4-acetoxy-5-(4-fluorophenoxy)-trans-2-pentene is substituted for the 1-(2-tetrahydropyranyloxy)-4-acetoxy-5-(4-fluorophenoxy)-pentane of Example 4, Step B-5. The product is obtained as a viscous oil.

Step A-5. Preparation of 4-Acetoxy-5-(4-fluorophenoxy)-trans-2-penten-1-ol Tosylate The synthesis of this compound is carried out by the procedure of Example 4, Step B-6 except that an equivalent quantity of 4-acetoxy-5-(4-fluorophenoxy)-trans-2-penten-1-ol is substituted for the 4-acetoxy-5-(4-fluorophenoxy)-1-pentanol of Example 4, Step B-6.

Step A-6. Preparation of 4-Acetoxy-5-(4-fluorophenoxy)-1-iodo-trans-2-pentene The synthesis of this compound is carried out by the procedure of Example 4, Step B-7 except that an equivalent quantity of 4-acetoxy-5-(4-fluorophenoxy)-trans-2-penten-1-ol tosylate is substituted for the 4-acetoxy-5-(4-fluorophenoxy)-1-pentanol tosylate of Example 4, Step B-7.

Step B. Preparation of Methyl 8-Acetyl-8-ethoxycarbonyl-12-acetoxy-13-(4-fluorophenoxy)tridec-10-trans-en-5-ynoate The synthesis of this compound is carried out by the procedure of Example 4, Step C except that an equivalent quantity of 4-acetoxy-5-(4-fluorophenoxy)-1-iodo-trans-2-pentene is substituted for the 4-acetoxy-5-(4-fluorophenoxy)-1-iodopentane of Example 4, Step C. The title compound is obtained similarly as a residual oil and is used in the next step without purification.

Step C. Preparation of 8-Acetyl-12-hydroxy-13-(4-fluorophenoxy)-tridec-10-trans-en-5-ynoic Acid The synthesis of this compound is carried out by the procedure of Example 4, Step D, except that an equivalent quantity of methyl 8-acetyl-8-ethoxycarbonyl-12-acetoxy-13-(4-fluorophenoxy)-tridec-10-trans-en-5-ynoate is substituted for the methyl 8-acetyl-8-ethoxycarbonyl-12-acetoxy-13-(4-fluorophenoxy)-5-tridecynoate of Example 4, Step D. The title compound is purified similarly by chromatography on silica gel with 2% methanol in chloroform as eluant.

Step D. Preparation of 8-Acetyl-12-hydroxy-13-(4-fluorophenoxy)-5-cis-10-trans-tridecadienoic Acid The synthesis of this compound is carried out by the hydrogenation procedure of Example 5 except that an equivalent quantity of 8-acetyl-12-hydroxy-13-(4-fluorophenoxy)-tridec-10-trans-en-5-ynoic acid is substituted for the 8-acetyl-12-hydroxy-13-(4-fluorophenoxy)-5-tridecynoic acid of Example 5. The title compound is purified similarly by column chromatography on silica gel.

EXAMPLE 9

Preparation of 8-Propionyl-12-hydroxy-13-(4-fluorophenoxy)-tridecanoic Acid

Step A. Preparation of Diethyl 2-Propionylazelate

The synthesis of this compound is carried out by the procedure of Example 4, Step A, except that an equivalent quantity of ethyl propionylacetate is substituted for the ethyl acetoacetate of Example 4, Step A, and an equivalent quantity of ethyl 7-bromoheptanoate is substituted for the methyl 7-bromo-5-heptynoate of Example 4, Step A. The product, a viscous oil, is used in the next step directly without distillation.

Step B. Preparation of Ethyl 8-Ethoxycarbonyl-8-propionyl-12-acetoxy-13-(4-fluorophenoxy)tridecanoate The synthesis of this compound is carried out by the procedure of Example 4, Step C except that an equivalent quantity of diethyl 2-propionylazelate is substituted for the methyl 8-ethoxycarbonyl-9-oxo-5-decynoate of Example 4, Step C. The product is used directly in the next step without purification.

Step C. Preparation of 8-Propionyl-12-hydroxy-13-(4-fluorophenoxy)-tridecanoic Acid The synthesis of this compound is carried out by the procedure of Example 4, Step D except that an equivalent quantity of ethyl 8-ethoxycarbonyl-8-propionyl-12-acetoxy-13-(4-fluorophenoxy)tridecanoate is substituted for the methyl 8-acetyl-8-ethoxycarbonyl-12-acetoxy-13-(4-fluorophenoxy)-5-tridecynoate of Example 4, Step D.

The product acid is purified by column chromatography on silica gel with 2% methanol in chloroform as eluant and is obtained as a yellowish, very viscous oil.

EXAMPLE 10

Preparation of 8-Acetyl-12-hydroxy-13-(4-tert-butyl-phenoxy)-tridecanoic Acid

A mixture of ethyl 8-acetyl-12,13-epoxytridecanoate (14.9 g., 0.05 mole), 4-tert-butylphenol (11.2 g., 0.075 mole), sodium hydroxide (7.0 g., 0.175 mole), water (30 ml.) and tetrahydrofuran (200 ml.) is stirred 4 hours at 40°–45°, 17 hours at 25° and one hour on the steam bath letting the tetrahydrofuran slowly boil away. The residue is treated with water and extracted with ether. The aqueous solution is acidified with hydrochloric acid. The oily product is taken up in ether. The ether is evaporated and the residue treated with a solution of 16.8 g. sodium bicarbonate in 275 ml. of water. The resulting solution is extracted twice with ether to remove the excess weakly acidic phenol. The aqueous solution is acidified, the product taken up in ether, washed with water and dried over sodium sulfate. The ether is evaporated leaving 10.2 g. of the crude title compound as a yellow viscous oil.

The product is purified by chromatography on a column containing 200 g. of silica gel made up in chloroform. The column is eluted with 2% methanol in chloroform. Fractions are combined and evaporated that contain a single component Rf 0.40 on silica gel thin layer plates with an eluant of chloroform-methanol-acetic acid, 95:4:1. The purified product weighs 5.1 g. and is a slightly yellowish viscous oil; pmr (CDCl$_3$) δ 1.30 (9H, s (CH$_3$)$_3$C); 2.10 (3H, s CH$_3$CO); 3.7–4.0 (3H, m CH$_2$O and CHO).

Anal. Calc'd. for C$_{25}$H$_{40}$O$_5$: C, 71.39; H, 9.59. Found: C, 71.16; H, 9.85.

EXAMPLE 11

Preparation of 8-Acetyl-12-hydroxy-13-(2-fluorophenoxy)-tridecanoic Acid

The synthesis of this compound is carried out by the procedure of Example 10 except that an equivalent amount of 2-fluorophenol is substituted for the 4-tert-butylphenol of Example 10. The title compound is obtained as a viscous oil after purification by silica gel column chromatography.

EXAMPLE 12

Preparation of 8-Acetyl-12-hydroxy-13-(4-methoxyphenoxy)-tridecanoic Acid

The synthesis of this compound is carried out by the procedure of Example 10 except that an equivalent amount of 4-methoxyphenol is substituted for the 4-tert-butylphenol of Example 10. The title compound is obtained as a viscous oil after purification by silica gel column chromatography.

EXAMPLE 13

Preparation of 8-Acetyl-12-hydroxy-13-phenoxytridecanoic Acid

The synthesis of this compound is carried out by the procedure of Example 10 except that an equivalent amount of phenol is substituted for the 4-tert-butyl-phenol of Example 10. The title compound is obtained as a colorless viscous oil after purification by silica gel column chromatography.

EXAMPLE 14

Preparation of 8-Acetyl-12-hydroxy-13-(3-trifluoromethylphenoxy)-tridecanoic Acid

Step A. Preparation of Ethyl 8-Acetyl-12-hydroxy-13-(3-trifluoromethylphenoxy)-tridecanoate Sodium (1.15 g., 0.05 mole) is dissolved in ethanol (60 ml.). 3-Trifluoromethylphenol (14.6 g., 0.09 mole) is added and then ethyl 8-acetyl-12,13-epoxytridecanoate (13.0 g., 0.0435 mole). The resulting solution is heated under reflux for 1.5 hour. It is then cooled and poured into 300 ml. of water. The oily product is taken up in ether, washed with 100 ml. of 5% sodium hydroxide solution, water and brine and dried over sodium sulfate. The ether is evaporated in vacuo leaving 17.4 g. of the title compound as a yellow oil. It is used in the next step without purification.

Step B. Preparation of 8-Acetyl-12-hydroxy-13-(3-trifluoromethylphenoxy)-tridecanoic Acid A solution of ethyl 8-acetyl-12-hydroxy-13-(3-trifluoromethylphenoxy)tridecanoate (17.4 g., 0.038 mole) and sodium hydroxide (4 g., 0.1 mole) in water (30 ml.) and methanol (120 ml.) is heated at 60° for 16 hours. Most of the methanol is then removed by distillation in vacuo. The residue is dissolved in 150 ml. of water and extracted with ether. The aqueous solution is acidified with concentrated hydrochloric acid. The oily product is taken up in ether and dried over sodium sulfate. Ether is evaporated in vacuo to leave the title compound as a viscous oil weighing 12.9 g. The product is purified by column chromatography on 200 g. of silica gel with 2% methanol in chloroform as eluant; pmr (CDCl$_3$) δ 2.10 (3H, s CH$_3$CO); 3.95 (3H, broad s CHO and CH$_2$O); 6.75 (2H, s OH and CO$_2$H).

Anal. Calc'd. for C$_{22}$H$_{31}$F$_3$O$_5$: C, 61.10; H, 7.23. Found: C, 60.83; H, 7.54.

Following the procedure of Example 14, Step A but substituting for the 3-trifluoromethylphenol used therein an equivalent amount of:
1. 3-bromophenol
2. 3-iodophenol
3. 3-chlorophenol
4. 3-methylphenol
5. 3-mesylphenol
6. 3-dimethylaminophenol
7. 3-ethylphenol
8. 3-methoxyphenol
9. 3-acetylphenol
10. 3-nitrophenol
11. 3-fluorophenol
12. 2,3-difluorophenol
13. 3,4-methylenedioxyphenol, or
14. 2,4-dichlorophenol,
and the reaction conducted and the product isolated as described, the product isolated in each instance is:
1. Ethyl 8-acetyl-12-hydroxy-13-(3-bromophenoxy)-tridecanoate
2. Ethyl 8-acetyl-12-hydroxy-13-(3-iodophenoxy)-tridecanoate
3. Ethyl 8-acetyl-12-hydroxy-13-(3-chlorophenoxy)-tridecanoate
4. Ethyl 8-acetyl-12-hydroxy-13-(3-methylphenoxy)-tridecanoate
5. Ethyl 8-acetyl-12-hydroxy-13-(3-mesylphenoxy)-tridecanoate
6. Ethyl 8-acetyl-12-hydroxy-13-(3-dimethylaminophenoxy)-tridecanoate
7. Ethyl 8-acetyl-12-hydroxy-13-(3-ethylphenoxy)-tridecanoate
8. Ethyl 8-acetyl-12-hydroxy-13-(3-methoxyphenoxy)-tridecanoate
9. Ethyl 8-acetyl-12-hydroxy-13-(3-acetylphenoxy)-tridecanoate
10. Ethyl 8-acetyl-12-hydroxy-13-(3-nitrophenoxy)-tridecanoate
11. Ethyl 8-acetyl-12-hydroxy-13-(3-fluorophenoxy)-tridecanoate
12. Ethyl 8-acetyl-12-hydroxy-13-(2,3-difluorophenoxy)-tridecanoate
13. Ethyl 8-acetyl-12-hydroxy-13-(3,4-methylenedioxyphenoxy)tridecanoate, and
14. Ethyl 8-acetyl-12-hydroxy-13-(2,4-dichlorophenoxy)-tridecanoate Following the procedure of Example 14, Step B, but substituting for the ethyl 8-acetyl-12-hydroxy-13-(3-trifluoromethylphenoxy)tridecanoate used therein an equivalent amount of each of the 14 compounds listed above and conducting the reaction and isolating the product essentially as described there is obtained:
1. 8-acetyl-12-hydroxy-13-(3-bromophenoxy)-tridecanoic acid
2. 8-acetyl-12-hydroxy-13-(3-iodophenoxy)tridecanoic acid
3. 8-acetyl-12-hydroxy-13-(3-chlorophenoxy)-tridecanoic acid
4. 8-acetyl-12-hydroxy-13-(3-methylphenoxy)-tridecanoic acid
5. 8-acetyl-12-hydroxy-13-(3-mesylphenoxy)tridecanoic acid
6. 8-acetyl-12-hydroxy-13-(3-dimethylaminophenoxy)-tridecanoic acid
7. 8-acetyl-12-hydroxy-13-(3-ethylphenoxy)tridecanoic acid
8. 8-acetyl-12-hydroxy-13-(3-methoxyphenoxy)-tridecanoic acid
9. 8-acetyl-12-hydroxy-13-(3-acetylphenoxy)-tridecanoic acid
10. 8-acetyl-12-hydroxy-13-(3-nitrophenoxy)-tridecanoic acid
11. 8-acetyl-12-hydroxy-13-(3-fluorophenoxy)-tridecanoic acid
12. 8-acetyl-12-hydroxy-13-(2,3-difluorophenoxy)-tridecanoic acid
13. 8-acetyl-12-hydroxy-13-(3,4-methylenedioxyphenoxy)-tridecanoic acid
14. 8-acetyl-12-hydroxy-13-(2,4-dichlorophenoxy)-tridecanoic acid.

EXAMPLE 15

Preparation of
8-Acetyl-12-hydroxy-13-benzyloxytridecanoic Acid

Step A. Preparation of Benzyl 8-Acetyl-12-hydroxy-13-benzyloxytridecanoate

Sodium hydride (0.04 mole) is added in portions with stirring to benzyl alcohol (25 ml.). To the resulting solution, ethyl 8-acetyl-12,13-epoxytridecanoate (0.02 mole) is added and the mixture allowed to stand 18 hours at 55°-60°. The reaction mixture is then cooled and treated with water. The organic layer is separated and dried over magnesium sulfate. Excess benzyl alcohol is removed by distillation in vacuo by means of the rotary evaporator at oil pump pressure. The residue consists mainly of the title compound and is used in the next step without purification.

Step B. Preparation of 8-Acetyl-12-hydroxy-13-benzyloxytridecanoic Acid

The synthesis of this compound is carried out by the hydrolytic procedure of Example 1, Step F, except that an equivalent quantity of benzyl 8-acetyl-12-hydroxy-13-benzyloxytridecanoate is substituted for the ethyl 8-acetyl-12-hydroxy-13-(4-fluorophenoxy)tridecanoate of Example 1, Step F. The title compound is purified by chromatography on silica gel with 3% methanol in chloroform as eluant.

EXAMPLE 16

Preparation of
8-Acetyl-12-hydroxy-13-furfuryloxytridecanoic Acid

Step A. Preparation of Ethyl 8-Acetyl-12-hydroxy-13-furfuryloxytridecanoate

The synthesis of this compound is carried out by the procedure of Example 1, Step E, except that an equivalent quantity of furfuryl alcohol is substituted for the 4-fluorophenol of Example 1, Step E.

Step B. Preparation of 8-Acetyl-12-hydroxy-13-furfuryloxytridecanoic Acid

The synthesis of this compound is carried out by the procedure of Example 1, Step F, except that an equivalent quantity of ethyl 8-acetyl-12-hydroxy-13-furfuryloxytridecanoate is substituted for the ethyl 8-acetyl-12-hydroxy-13-(4-fluorophenoxy)-tridecanoate of Example 1, Step F. The title compound is purified by chromatography on silica gel and is obtained as a yellow viscous oil.

EXAMPLE 17

Preparation of 8-Acetyl-12-hydroxy-13-(3-pyridyloxy)-tridecanoic Acid

Step A. Preparation of Ethyl 8-Acetyl-12-hydroxy-13-(3-pyridyloxy)tridecanoate The synthesis of this compound is carried out by the procedure of Example 1, Step E, except that an equivalent quantity of 3-hydroxypyridine is substituted for the 4-fluorophenol of Example 1, Step E.

Step B. Preparation of 8-Acetyl-12-hydroxy-13-(3-pyridyloxy)tridecanoic Acid The synthesis of this compound is carried out by the procedure of Example 1, Step F, except that an equivalent quantity of ethyl 8-acetyl-12-hydroxy-13-(3-pyridyloxy)tridecanoate is substituted for the ethyl 8-acetyl-12-hydroxy-13-(4-fluorophenoxy)tridecanoate of Example 1, Step F.

EXAMPLE 18

Preparation of 8-Acetyl-12-hydroxy-13-(4-fluorophenylthio)-tridecanoic Acid

Step A. Preparation of Ethyl 8-Acetyl-12-hydroxy-13-(4-fluorophenylthio)tridecanoate The synthesis of this compound is carried out by the procedure of Example 1, Step E, except that an equivalent quantity of 4-fluorothiophenol is substituted for the 4-fluorophenol of Example 1, Step E.

Step B. Preparation of 8-Acetyl-12-hydroxy-13-(4-fluorophenylthio)-tridecanoic Acid The synthesis of this compound is carried out by the procedure of Example 1, Step F, except that an equivalent quantity of ethyl 8-acetyl-12-hydroxy-13-(4-fluorophenylthio)tridecanoate is substituted for the ethyl 8-acetyl-12-hydroxy-13-(4-fluorophenoxy)tridecanoate of Example 1, Step F.

EXAMPLE 19

Preparation of 8-Acetyl-12-hydroxy-13-propoxytridecanoic acid

A mixture of ethyl 8-acetyl-12,13-epoxytridecanoate (14.9 g., 0.05 mole), propanol (60 ml.), sodium hydroxide (6.0 g., 0.15 mole) and water (15 ml.) is stirred 4 hours at 40°-45° and then heated 1 hour on the steam bath. The mixture is cooled, treated with water (250 ml.) and extracted with ether. The aqueous solution is acidified with hydrochloric acid. The oily product is taken up in ether, washed with water, and dried over sodium sulfate. Evaporation of the ether leaves the title compound as a pale yellow oil. Purification is effected by column chromatography on silica gel with 2% methanol in chloroform as the eluant.

By the use of the same procedure but substituting for the propanol used above
 ethanol
 n-butanol
 sec-butanol
 3,3,3-trifluoro-1-propanol or
 propyl mercaptan
there is obtained in each instance
 8-acetyl-12-hydroxy-13-ethoxytridecanoic acid
 8-acetyl-12-hydroxy-13-butoxytridecanoic acid
 8-acetyl-12-hydroxy-13-(2-methylpropoxy)tridecanoic acid
 8-acetyl-12-hydroxy-13-(3,3,3-trifluoropropoxy)-tridecanoic acid or
 8-acetyl-12-hydroxy-13-propylthiotridecanoic acid.

EXAMPLE 20

Preparation of Methyl 8-Acetyl-12-hydroxy-13-(4-fluorophenoxy)tridecanoate

A solution of diazomethane (approximately 2.5 g., 0.06 mole) in ether (100 ml.) is mixed with a solution of 8-acetyl-12-hydroxy-13-(4-fluorophenoxy)tridecanoic acid (11.5 g., 0.03 mole) in ether (50 ml.). The resulting solution is allowed to stand 4 hours at room temperature. Acetic acid is then added to destroy the excess diazomethane and the solution is washed with dilute sodium bicarbonate solution and water and dried over sodium sulfate. Evaporation of volatile materials at reduced pressure yields the title ester as a yellow viscous oil.

EXAMPLE 21

Preparation of 8-Acetyl-12-acetoxy-13-(4-fluorophenoxy)-tridecanoic Acid

A mixture of 8-acetyl-12-hydroxy-13-(4-fluorophenoxy)tridecanoic acid (9.5 g., 0.025 mole) and acetic anhydride (6.1 g., 0.06 mole) is heated at 60° for 18 hours. The mixture is then cooled and dissolved in 80 ml. of ether. The solution is extracted with an ice-cold solution of 8 g. of sodium hydroxide in 150 ml. of water. The basic solution is separated and acidified with concentrated hydrochloric acid. The oily acid that separates is taken up in ether, washed with water and dried over sodium sulfate. The ether is evaporated to leave the crude product as a viscous yellow oil.

The product is purified by chromatography on a column containing 200 g. of silica gel and with 2% methanol in chloroform as the eluting solvent. The title compound when purified is a light yellow viscous oil.

EXAMPLE 22

Preparation of N-(2-Dimethylaminoethyl)-8-acetyl-12-hydroxy-13-(4-fluorophenoxy)tridecanamide A solution of 8-acetyl-12-hydroxy-13-(4-fluorophenoxy)tridecanoic acid (3.82 g., 10 millimole), Example 1, Step F, triethylamine (1.74 ml., 12.5 millimole) and distilled water (18 ml., 1.0 mole) in acetonitrile (100 ml.) is treated with N-t-butyl-5-methylisoxazolium perchlorate (3.0 g., 12.5 millimole). The resulting solution is evaporated in vacuo (water aspirator) at 20°-23° for 4 hours providing a tacky residue which is triturated with water (150 ml.) at 0°-5° for 15 minutes. After decanting the aqueous phase, the oily residue is dissolved in benzene-ether [(1:1), 200 ml.]. The organic extract is dried over sodium sulfate, filtered and evaporated in vacuo at 35°-40° providing the desired "active ester", N-t-butyl-3-(8-acetyl-12-hydroxy-13-(4-fluorophenoxy)-tridecanoyloxy)crotonamide, as a pale yellow oil.

A solution of 2-dimethylaminoethylamine (0.88 g., 10 millimole) in acetonitrile (25 ml.) is added to a solution of the "active ester" in acetonitrile (25 ml.) providing a clear solution which is stirred at 25° for 17 hours. The solvent is removed in vacuo at 40°-50° leaving a residual oil which is partitioned between ether (200 ml.) and water (2 × 100 ml.). The organic extract is washed with saturated brine (2 × 100 ml.), dried over sodium sulfate, filtered and evaporated in vacuo at 40°-50° providing a tan, crude oil.

The oil is partitioned between 5% hydrochloric acid (100 ml.) and ether (2 × 100 ml.). The aqueous acid phase is slowly basified with sodium bicarbonate (16.8 g., 0.2 mole), then with 40% aqueous sodium hydroxide (10 ml.) providing a heterogeneous mixture which is extracted with ether (200, 100 ml.). The organic extract is washed with saturated brine (200 ml.), dried over sodium sulfate, filtered and evaporated in vacuo at 40°-50° leaving the title compound as a pale yellow oil.

EXAMPLE 23

CAPSULE FORMULATION

| | |
|---|---|
| 8-(1-hydroxyethyl)-12-hydroxy-13-(4-fluorophenoxy)-5-cis-tridecenoic acid | 50 gm. |
| Stearic acid (U.S.P. triple pressure) | 125 gm. |
| Pluronic F-68 | 7.5 gm. |
| Corn starch | 125 gm. |

The stearic acid and pluronic are united in a vessel and melted using a water bath at 60°-65° C. The heating is discontinued and the 8-(1-hydroxyethyl)-12-hydroxy-13-(4-fluorophenoxy)-5-cis-tridecenoic acid is dispersed into the mixture and the corn starch is added with stirring which is continued until the mixture cools to ambient temperature. The mixture is reduced to granules by screening and placed in a number 0 hard gelatin containing 307.5 mg. of total solids and 50 mg. of 8-(1-hydroxyethyl)-12-hydroxy-13-(4-fluorophenoxy)-5-cis-tridecenoic acid per capsule.

What is claimed is:
1. The compound of the formula

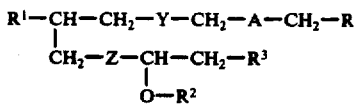

wherein
R is selected from the group consisting of carboxy and a carboxy salt, and alkoxycarbonyl (—COOAlk) wherein Alk is alkyl having 1-10 carbon atoms;
$R^1$ is selected from the group consisting of acetyl, propionyl, 1-hydroxyethyl, 1-hydroxypropyl and hydroxymethyl;
$R^2$ is hydrogen or lower alkanoyl;
$R^3$ is O—$R^6$ or wherein $R^6$ is
pyridyl, pyrimidinyl, furfuryl, or thenyl;
A is methylene (—$CH_2$—);
Y is selected from the group consisting of ethylene, vinylene, or ethynylene;
and
Z is selected from the group consisting of ethylene, vinylene or ethynylene.

2. The compound of claim 1 wherein $R^1$ is selected from 1-hydroxyethyl, 1-hydroxypropyl and hydroxymethyl.

3. The compound of claim 1 wherein $R^1$ is selected from acetyl and propionyl.

4. The compound of claim 3 wherein $R^1$ is propionyl.

5. The compound of claim 3 wherein $R^1$ is acetyl.

6. The compound of claim 3 wherein Y is vinylene or ethynylene.

7. The compound of claim 5 wherein Z is vinylene or ethynylene.

8. The compound of claim 3 wherein $R^3$ is 2-furfuryloxy or 3-pyridyloxy.

9. The compound of claim 8 which is 8-acetyl-12-hydroxy-13-furfuryloxytridecanoic acid.

10. The compound of claim 8 which is 8-acetyl-12-hydroxy-13-(3-pyridyloxy)tridecanoic acid.

* * * * *